United States Patent

Koyama et al.

Patent Number: 6,126,294
Date of Patent: Oct. 3, 2000

[54] PORTABLE LIGHT IRRADIATION APPARATUS

[75] Inventors: Emi Koyama, Osaka; Hozumi Matsubara, Hirakata; Hiroyuki Nishimura, Yawata; Toshio Nakano, Osaka; Yoshimasa Tanaka, Hikone; Suehiro Morita, Sabae, all of Japan

[73] Assignee: Matsushita Electric Works, Ltd., Osaka, Japan

[21] Appl. No.: 09/319,932

[22] PCT Filed: Oct. 20, 1998

[86] PCT No.: PCT/JP98/04737
§ 371 Date: Jun. 17, 1999
§ 102(e) Date: Jun. 17, 1999

[87] PCT Pub. No.: WO99/20333
PCT Pub. Date: Apr. 29, 1999

[30] Foreign Application Priority Data

Oct. 20, 1997 [JP] Japan .................................. 9-287375
Mar. 26, 1998 [JP] Japan .................................. 10-080015

[51] Int. Cl.⁷ ............................................... F21V 21/084
[52] U.S. Cl. .......................... 362/105; 362/103; 362/223; 362/285; 362/287; 362/427
[58] Field of Search ...................... 362/105, 106, 362/558, 103, 223, 572, 285, 287, 288, 427, 1; 2/422

[56] References Cited

U.S. PATENT DOCUMENTS

| | | |
|---|---|---|
| 4,310,732 | 1/1982 | Stearn et al. .............................. 379/430 |
| 4,593,683 | 6/1986 | Blaha ....................................... 210/331 |
| 4,737,972 | 4/1988 | Schoolman ................................ 378/41 |
| 4,875,233 | 10/1989 | Derhaag et al. ......................... 379/430 |
| 5,430,620 | 7/1995 | Li et al. .................................. 362/572 |
| 5,564,128 | 10/1996 | Richardson ................................ 2/422 |

Primary Examiner—Sandra O'Shea
Assistant Examiner—Ali Alavi
Attorney, Agent, or Firm—Arent Fox Kitner Plotkin & Kahn, PLLC

[57] ABSTRACT

A portable light irradiation device for providing a stimulus of light to the eyes of user is used to regulate biological rhythm and improve awakening level of the user. This device includes an elongate illumination unit for irradiating the light to the user's eyes, a pair of pads adapted to be fitted to sides of the user's head, a headband adapted to be fitted to a top of the user's head and coupled to the pads at opposite ends thereof, and a supporting arm extending from at least one of the pads for supporting the illumination unit at the forward end thereof such that the illumination unit can be disposed in front of the eyes of the user wearing the light irradiation device. The supporting arm is slidably supported to the pad at the rear end thereof such that a projection length of the supporting arm against the pad is adjustable. By this component, since a distance between the user's eyes and the illumination unit can be suitably determined, it is possible to effectively provide an optical medical treatment to the user by use of the light irradiation device.

14 Claims, 14 Drawing Sheets

PORTABLE LIGHT IRRADIATION APPARATUS

BACKGROUND OF THE INVENTION

1. Field of the Invention

The present invention relates to a portable light irradiation device, which can be used to stimulate the eyes of user with light to regulate biological rhythm and improve awakening level of the user.

2. Disclosure of the Prior Art

As a medical treatment for wrong biological rhythm (or biological clock) or wrong sleeping-awakening rhythm of a subject, irradiating a high illumination light to the subject over a couple of hours has been well known in the past. This medical treatment is effective for a biological rhythm trouble with abnormal actions that is often observed on dementia patients, seasonal emotion trouble, endogenous depression, or a sleeping-awakening rhythm trouble. In addition, the medical treatment is effective for a fatigue caused by night work or jet lag at overseas travel.

In this optical medical treatment, the patient's or subject's eyes are stimulated with a high illumination light provided from an artificial light source at a time interval determined according to a degree of the wrong biological rhythm. When the condition of a patient is, for example, a slight seasonable emotion trouble or sleeping-awakening rhythm trouble, and the patient can normally spend daily life, it is preferred that the patient continues the optical medical treatment with use of a portable light irradiation device for irradiating the light to the patient's eyes, while spending the daily life.

For example, WO 89/08476 discloses a portable light irradiation device of this type. This device includes a headband adapted to be fitted on the head of user, a pair of supporting arms extending forwardly of the user from opposite ends of the headband, an illumination unit supported by the supporting arms and arranged in front of the eyes of the user, and a battery for supplying electric power to the illumination unit. By the way, in the normal optical medical treatment, it is required to irradiate the high illumination light to the patient over at least 30 minutes, and preferably about 2 hours. Therefore, to improve the effect of the optical medical treatment, it is important to suitably determine factors such as the setting position of the illumination unit to the user and the fitting state of the light irradiation device to the user's head with respect to the individual user. When these factors are not suitably set, the user may receive psychological unpleasant feeling or physically oppressive sensation during the optical medical treatment. Consequently, there is a problem that the effect of the optical medical treatment can not be sufficiently achieved.

SUMMARY OF THE INVENTION

Therefore, an object of the present invention is to provide a portable light irradiation device for improving the above problems. That is, this light irradiation device includes an illumination unit of an elongate shape for irradiating a light to the eyes of user, a pair of pads adapted to be fitted on both sides of the head of the user, a headband adapted to be fitted to a top of the user's head, which is coupled to the pads at opposite ends thereof, and a supporting arm extending from at least one of the pads to support the illumination unit at a forward end thereof so that the illumination unit can be disposed in front of the eyes of the user wearing the light irradiation device. The present invention is characterized in that the supporting arm is slidably supported to the pad at a rear end thereof such that a projection length of the supporting arm against the pad is adjustable. Thereby, it is possible to suitably determine a distance between the user eyes and the illumination unit, and also effectively provide an optical medical treatment without psychological unpleasant feeling or physically oppressive sensation caused to the user by unsuitable setting of the illumination unit.

It is preferred that the light irradiation device has a click mechanism for adjusting the projection length of the supporting arm against the pad in a stepwise manner. This click mechanism includes a click spring member supported by the pad, and a slit formed in the supporting arm along a longitudinal direction of the supporting arm. The slit has a plurality of pockets arranged along the longitudinal direction. The click spring member is movable within the slit so as to selectively make a click engagement with one of the pockets. By this click mechanism, it is possible to readily determine a suitable distance between the illumination unit and the eyes of the user wearing the light irradiation device of the present invention.

In addition, it is preferred that the supporting arm is rotatably supported to the pad at the rear end thereof such that a projection direction of the supporting arm against the pad is adjustable. In this case, it is possible to irradiate the light from the illumination unit to the user's eyes from a suitable direction that does not give the psychological unpleasant feeling to the user.

In a further preferred embodiment of the present invention, a click mechanism for adjusting both of the projection length of the supporting arm against the pad and the projection direction of the supporting arm against the pad in a stepwise manner. The click mechanism includes a click spring having a pair of first projections in a first direction and a pair of second projections in a second direction perpendicular to the first direction. The click spring is made of an elastic material so that a distance between the first projections and a distance between the second projections are variable. A coupling member supported by the pad has a pair of arcuate grooves formed around a horizontal axis extending between the pads. Each of the arcuate grooves has a plurality of first pockets, so that each of the first projections of the click spring selectively makes a click-engagement with one of the first pockets of the arcuate groove. In addition, the supporting arm has a slit formed in the supporting arm along a longitudinal direction of the supporting arm. The slit has a plurality of pairs of second pockets, so that the second projections of the click spring selectively make a click-engagement with one pair of the second pockets. By this click mechanism, it is possible to readily determine a suitable distance between the illumination unit and the users eyes, and irradiate the light of the illumination unit to the user's eyes from a suitable direction that does not give the psychological unpleasant feeling to the user wearing the light irradiation device of the present invention. Additionally, even when the optical medical treatment is periodically performed to the user, it is not necessary to search the suitable setting position of the illumination unit for the individual user every medical treatment. In other words, it is possible to readily and speedily set the illumination unit to the suitable position by use of the click mechanism.

It is further preferred that the supporting arm and the headband are rotatably supported to the pad to obtain a compact folding state of the light irradiation device. By use of this folding mechanism, since the light irradiation device is handy to carry during oversea travel, the usefulness of the light irradiation device will be increased.

It is preferred that the supporting arm described above of the light irradiation device is provided with a pair of supporting arms extending from the pads to opposite end portions of the illumination unit, and each of the supporting arms has a flexible portion so that a spacing between the supporting arms is variable in accordance with a spacing between the pads. In this case, it is possible to comfortably fit the light irradiation device to the user, for example, even the user with a relatively large head size, irrespective of individual difference of head size of the user. It is also preferred that the headband is slidably supported to the pads at opposite ends thereof such that an effective length defined as a length of the headband extending between the pads is adjustable. By adjusting the effective length of the headband, the headband can be just fitted to the top of the user's head. Moreover, it is preferred that the light irradiation device of the present invention includes an auxiliary headband adapted to be fitted to a rear portion of the user's head, and the auxiliary headband is swingably supported to the pads at opposite ends thereof. The user might feel a weight of the light irradiation device in the vicinity of the forehead due to the weight of the illumination unit. By use of the auxiliary headband, a part of the weight of the light irradiation device can be borne by the rear portion of the user's head. Therefore, it is usefull to prevent the occurrence of unpleasant oppressive feeling during the optical medical treatment. It is particularly preferred that the auxiliary headband is supported to the pads through spring members, and the spring members provide a spring bias to the auxiliary headband in a direction away from the headband. Consequently, it is possible to easily fit the auxiliary headband to the rear portion of the user's head.

In addition, it is preferred that the auxiliary band is fixable to the supporting arm at a position, where the auxiliary headband is spaced away from the headband by a horizontal distance so as to extend substantially parallel to the headband. When the auxiliary headband is supported through the spring member, there is a possibility that displacement of the auxiliary headband by the spring member occurs at the folding state of the light irradiation device. In this case, since the auxiliary headband is locked at the above-explained position by the supporting arm, it is possible to prevent such a displacement of the auxiliary headband.

As a preferred embodiment of the illumination unit used in the light irradiation device of the present invention, it is preferred that the illumination unit has a housing in which a light source, reflector for reflecting light provided from the light source, light diffusing member for diffusing reflection from the reflector to form a diffusion light and providing the diffusion light to the user's eye, and a printed board including a lighting circuit for the light source are incorporated. In addition, it is preferred that the reflector, the light diffusing member and the light source are detachable to the housing, and the light source is detachably connected to the lighting circuit by use of a plug-socket structure. When using this illumination unit, there is an advantage that the user can exchange the light diffusing member, the reflector and the light source, for maintenance by itself.

Further features of the present invention and effects brought thereby will be understood in detail from the following descriptions of preferred embodiments of the present invention referring to the attached drawings.

DETAILED DESCRIPTION OF PREFERRED EMBODIMENTS

A portable light irradiation device of a first embodiment of the present invention is explained in detail.

Figure 1:
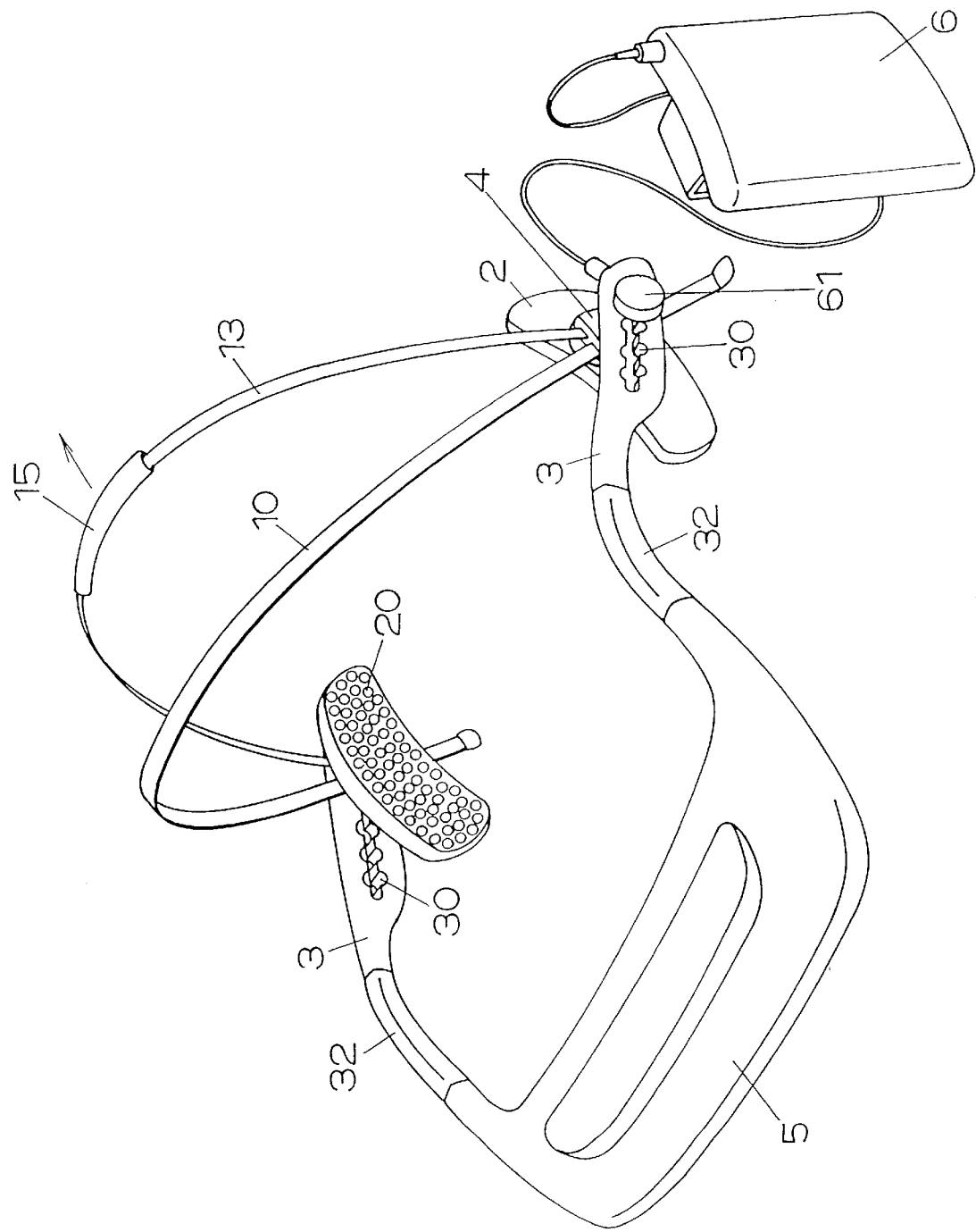
FIG. 1 is a perspective view of a light irradiation device of a first embodiment of the present invention.

As shown in FIG. 1, the light irradiation device includes a headband 10, auxiliary headband 13, a pair of pads 2, a pair of supporting arms 3, and an illumination unit 5 connected to the supporting arms. The numeral 6 designates a battery for supplying electric power to the illumination unit 5.

Figure 2:
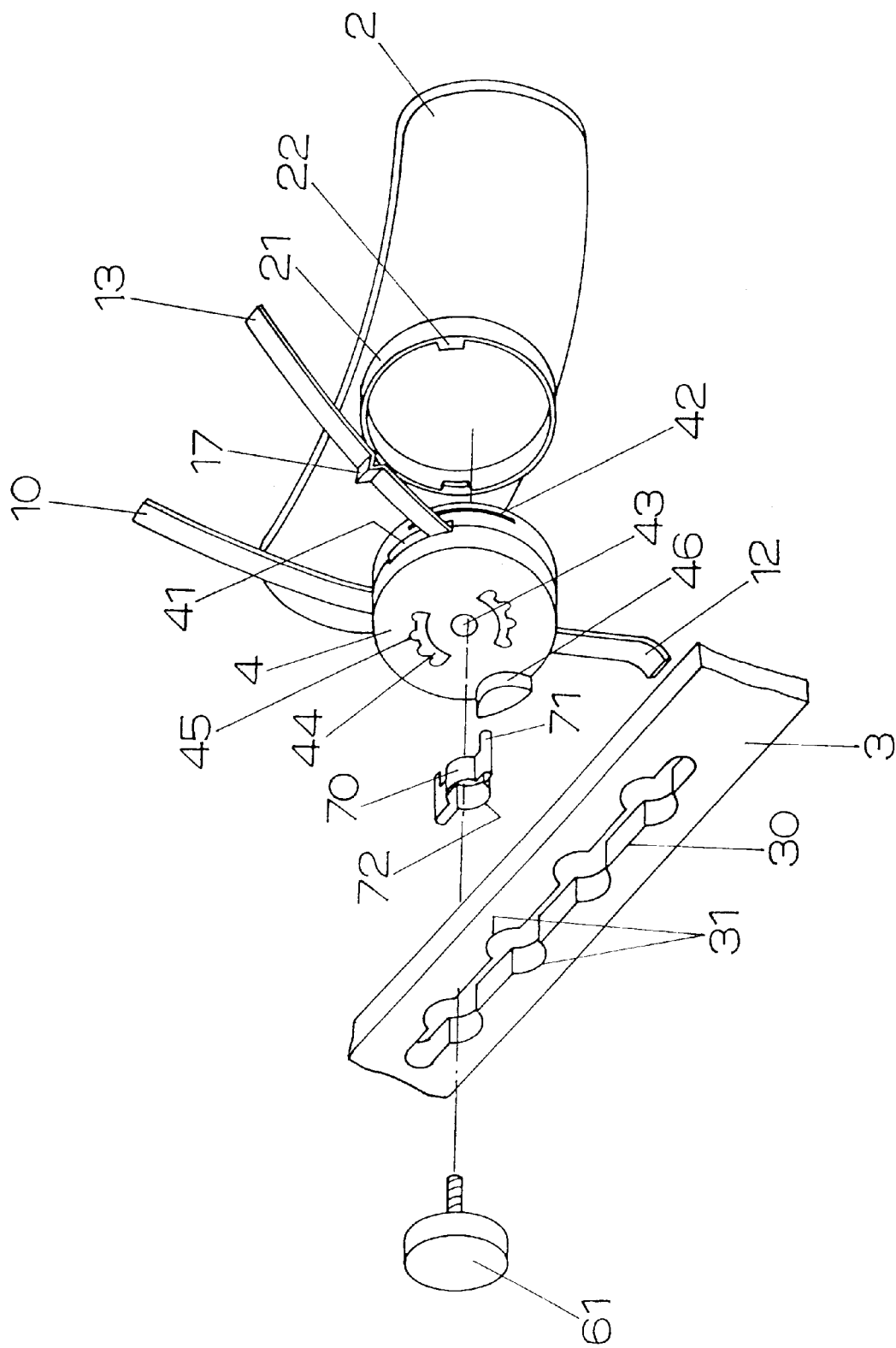
FIG. 2 is an exploded perspective view of a mechanism for coupling a supporting arm to a pad.
Figures 3A, 3B:
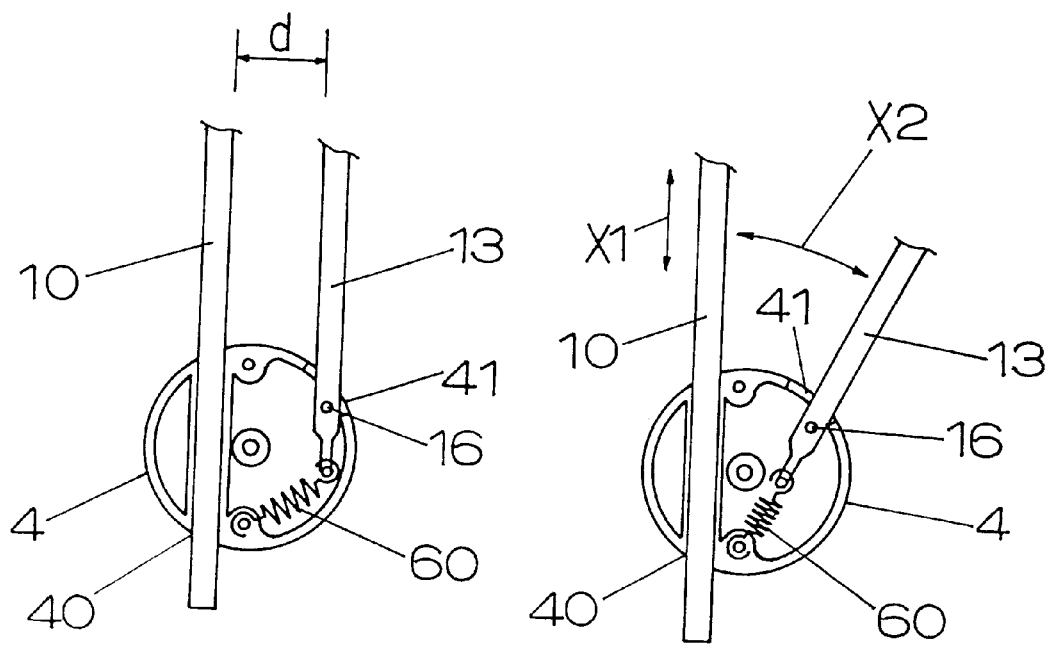
FIGS. 3A and 3B are cross-sectional views of a mechanism for coupling an auxiliary headband to a supporting member.

The headband 10 is an elongate spring plate member, which is arcuately bent to provide a spring force such that both of the pads 2 are pressed on both sides of the head of user wearing the light irradiation device with just the right amount of holding pressure. The headband 10 is movably supported to a supporting member 4 of a substantially cylindrical shape. That is, as shown in FIG. 2 and FIG. 3A, each of opposite end portions of the headband 10 passing a through hole 40 of the supporting member 4 is supported by friction with the supporting member. Therefore, the headband 10 is slidably supported to the supporting member 4 in a direction shown by the arrow X1 in FIG. 3A, so that an effective length defined as a length of the headband 10 extending between the pads 2 is adjustable. In FIG. 2, the numeral 12 designates a stopper formed at each end of the headband to avoid falling of the headband 10 from the supporting member 4.

Figure 4:
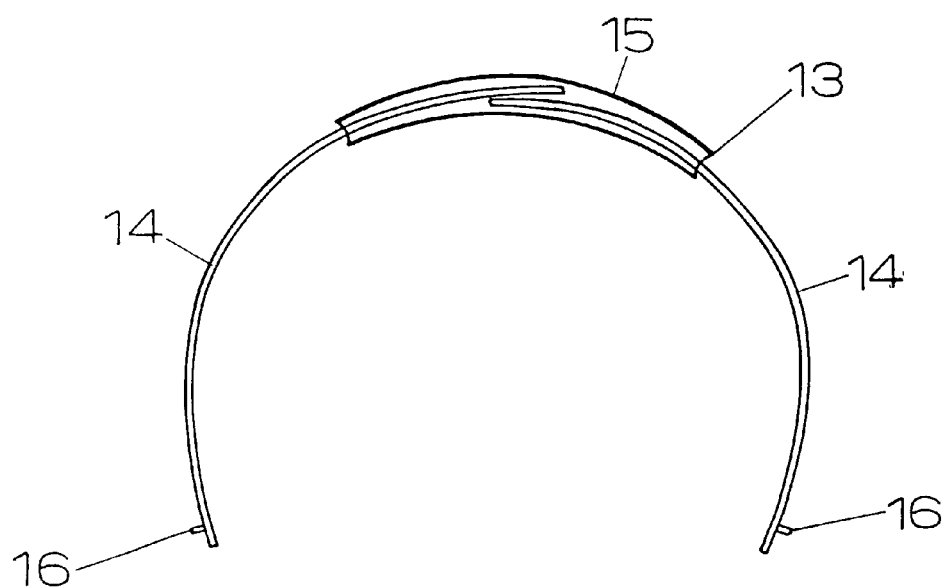
FIG. 4 is a partially transparent plan view of the auxiliary headband.

On the other hand, as shown in FIG. 4, the auxiliary headband 13 includes a pair of elongate spring strips as arcuate arms 14 and a tubular member 15 for coupling the arcuate arms each other. That is, one end of the respective arcuate arm inserted into the tubular member 15 is slidably supported to the tubular member so that a projection length of the arcuate arm from the tubular member is adjustable. The auxiliary headband 13 is attached to the supporting member 4 such that a spring bias is applied to the auxiliary headband in a direction away from the headband 10. That is, each end of the auxiliary headband 13 inserted into the supporting member 4 through a slit 41 is coupled to the supporting member through a spring 60. A shaft 16 projected on the respective end of the auxiliary headband 13 is engaged to the supporting member such that the auxiliary headband is swingable about the axis of the shaft 16, as shown by the arrow X2 in FIG. 3A. Moreover, as shown in FIG. 3B, a length of the slit 41 is determined such that the auxiliary headband 13 can not swing toward the headband 10 beyond a substantially vertical position. Since the spring bias is applied to the auxiliary headband 13 by the spring 60, the auxiliary headband is stable at a position shown in FIG. 3A, where the auxiliary headband is in line with the axis of the spring 60. As shown in FIG. 3B, to provide a required distance d between the headband 10 and the auxiliary headband 13 at the vertical position, the shaft 16 of the auxiliary headband 13 is supported at a position horizontally spaced from the headband 10. This is useful to avoid a situation that the user's hair is accidentally caught between the auxiliary headband and the headband. By the way, most of the weight of the light irradiation device lies at a side of the illumination unit 5 (i.e., the front side of the user). By fitting the auxiliary headband to the rear portion of the head, it is possible to suitably keep the weight balance between the front side and the rear side of the light irradiation device, and just fit the light irradiation device to the user's head.

The pads 2 are used to provide comfortable fitting of the light irradiation device to the user. A first surface 20 of the respective pad 2 contacts the side portion of the user's head by the spring force of the headband 10. As shown in FIG. 2, the opposite surface of the pad 2 is provided with a circular wall 21 for receiving the supporting member 4 of the cylindrical shape therein. A pair of projections 22 formed at the edge of the circular wall 21 are engaged to grooves 42 formed at the periphery of the supporting member 4. Since the projections 22 are movable in the grooves 42, it is possible to rotate the pad 2 along the sidewall of the supporting member 4. That is, it is possible to suitably adjust the fitting position of the pad 2 on the side portion of the head without changing the fitting positions of the auxiliary headband 13 and headband 10 to the user. In place of the pad 2 shown in the attached figures, a sponge pad (not shown) having the substantially same diameter as the supporting member 4 may be used. Each of end portions of the supporting arms 3 is supported to the supporting member 4 through a click spring 70 such that a projection length of the supporting arm against the pad 2 fitted to the side portion of the user's head and a projecting direction of the supporting arm against the pad are adjustable. As shown in FIG. 2, the click spring 70 is a spring member having a horizontally-opposed first projection pair 71 and a vertically-opposed second projection pair 72. The click spring 70 can be made of an elastic material so that distances between the first projections and between the second projections are variable by elastic deformation. For example, a synthetic resin having elasticity such as POM may be used. The supporting member 4 is formed in the opposed surface to the surface facing the pad 2 with a screw hole 43 and a pair of first click grooves 44 arcuately formed around the screw hole. The first click groove 44 has a plurality of pockets 45. Each of the first projections 71 of the click spring 70 selectively engages in one of the pockets 45 of the first click groove 44. On the other hand, the end portion of the supporting arm 3 is formed with a second click groove 30 having a plurality of pocket pairs 31 arranged in the longitudinal direction of the supporting arm. The second projections 72 of the click spring 70 selectively engage in one pair of the pocket pairs 31 of the second click groove 30.

Figure 5A:
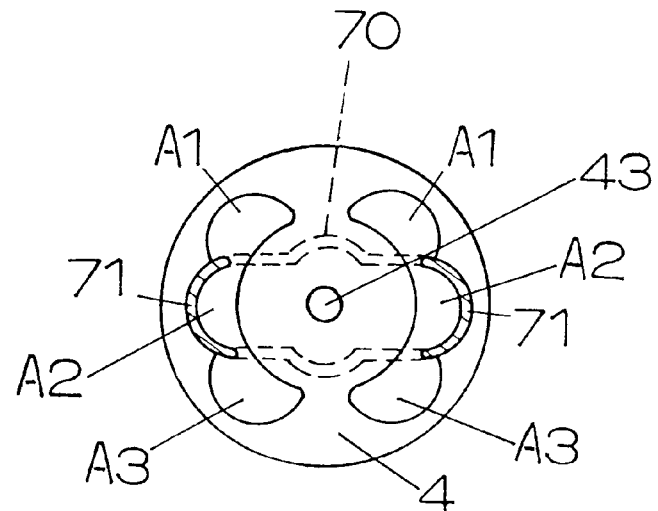
FIGS. 5A to 5C are diagrams illustrating a mechanism for making a click engagement between a click spring member and the supporting member.
Figure 5B:
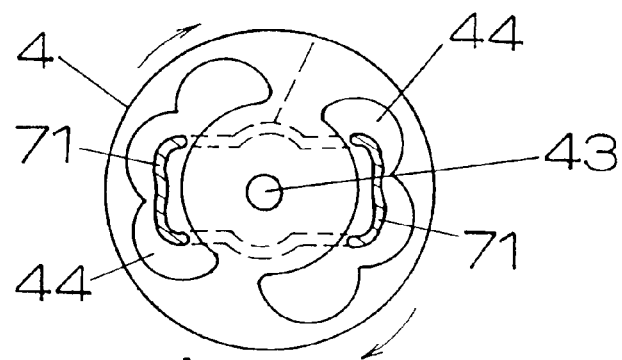
Figure 5C:
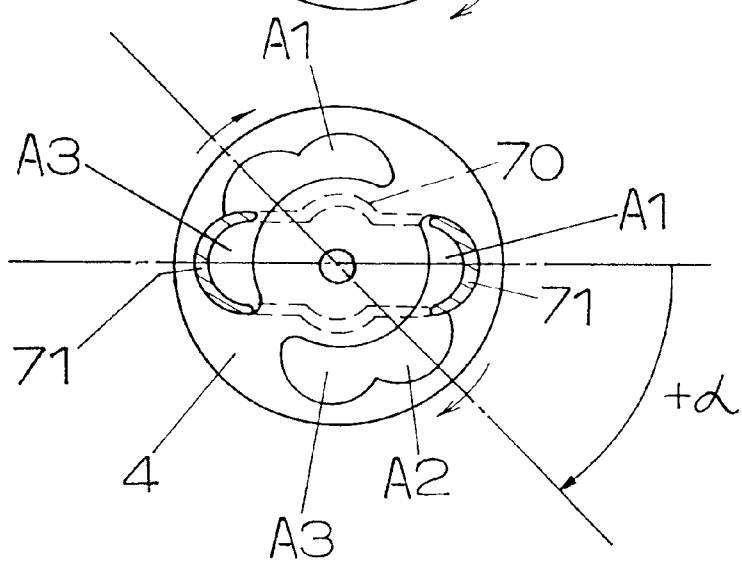

As an example, with respect to the first click groove 44 having three pockets (A1, A2, A3), a click mechanism for selectively determining the projecting direction of the supporting arm 3 from three directions is explained referring to FIGS. 5A to 5C. In FIG. 5A, each of the first projections 71 of the click spring 70 engages in the pocket A2 of the respective first click groove 44. When the supporting member 4 is rotated in a direction shown by the arrows in FIG. 5B, the first projection 71 of the click spring 70 receives elastic deformation during the travel between the adjacent pockets of the first click groove 44. As shown in FIG. 5C, when the supporting member 4 is further rotated, one of the first projections 71 engages in the pocket A3 of the first click groove 44, and the other one of the first projections engages in the pocket A1 of the first click groove, so that the elastic deformation of the click spring is released. Thus, it is possible to rotate the supporting member 4 against the click spring 70 by an angle of +α. Of course, when the supporting member 4 is rotated in the reverse direction, it is possible to rotate the supporting member 4 against the click spring 70 by an angle of −α. Since the second projections 72 of the click spring 70 engages in the second click groove 30 of the supporting arm 3, the rotation of the click spring 70 relative to the supporting member 4 means changing the projecting direction of the supporting arm 3 against the supporting member 4. As a result, the projecting direction of the supporting arm can be adjusted in a stepwise manner by use of the click mechanism between the first projections 71 and the first click grooves 44.

Figure 6A:
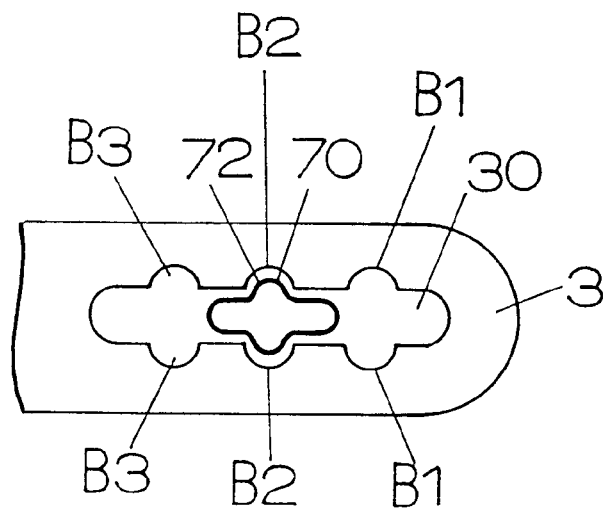
FIGS. 6A to 6C are diagrams illustrating a mechanism for making a click engagement between the click spring member and the supporting arm.
Figure 6B:
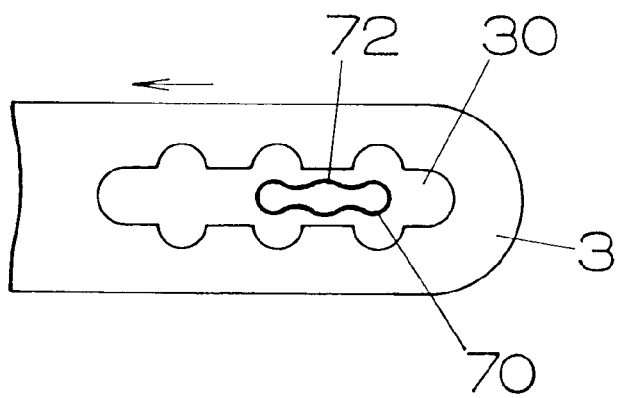
Figure 6C:
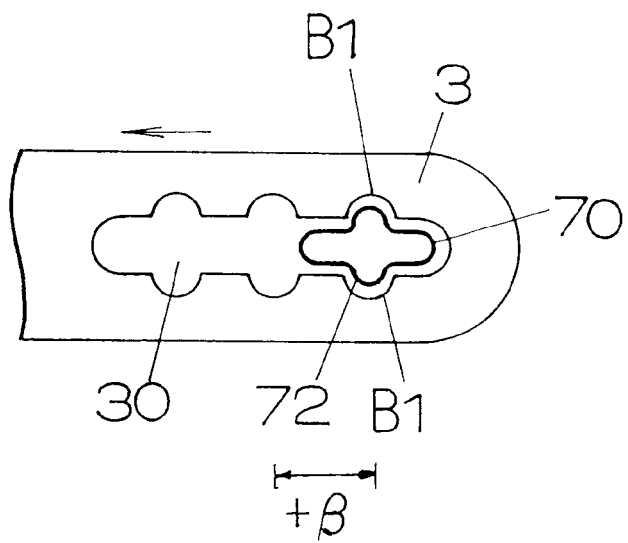

On the other hand, with respect to the second click groove 30 having three pocket pairs (B1, B2, B3), a click mechanism for selectively determining the projection length of the supporting arm 3 from three lengths is explained referring to FIGS. 6A to 6C. In FIG. 6A, the second projections 72 of the click spring 70 engages in the pocket pair B2 positioned at the center of the second click groove 30. When the supporting arm 3 is moved in a direction shown by the arrow in FIG. 6B, the second projections 72 of the click spring 70 receive elastic deformation during the travel between the adjacent pocket pairs of the second click groove 44. As shown in FIG. 6C, when the supporting arm 3 is further moved along the direction, the second projections 72 engages in the adjacent pocket pair B1 of the second click groove 30, so that the elastic deformation of the click spring is released. Since the direction of the elastic deformation of the first projections 71 is substantially orthogonal relation with the direction of the elastic deformation of the second projections 72, one of the click mechanisms can stably function independently from the other click mechanism. Thus, it is possible to move the supporting arm 3 against the click spring 70 by a distance of +β. Of course, when the supporting arm 3 is moved in the reverse direction, it is possible to move the supporting arm 3 against the click spring 70 by a distance of −β. As a result, the projection length of the supporting arm 3 can be adjusted in a stepwise manner by use of the click mechanism between the second projections 72 and the second click groove 30.

In conclusion, by introducing these click mechanisms, an angle of the illumination unit 5 to the user's eyes, and a space between the illumination unit and the user's eyes can be suitably determined to the individual user. In addition, it is worthy of note that the position of the illumination unit 5 to the user's eyes can be adjusted without changing the adequate positions of the auxiliary headband 13, the headband 10 and the pads 2 fitted on the user's head. Additionally, when periodically performing the optical medical treatment to the user by use of the light irradiation device, it is not necessary to repeat an operation of determining the most suitable position of the illumination unit 5 to the user every medical treatment. In other words, it is possible to easily reproduce the most suitable position of the illumination unit 5 by use of the above-explained click mechanisms.

As shown in FIG. 2, the pads 2, the supporting member 4, and the supporting arm 3 are coupled each other by use of a screw 61 passing the second click groove 30 of the supporting arm 3 and the inside of the click spring 70. That is, the supporting arm 3 is supported between a head of the screw 61 and the supporting member 4. In FIG. 2, the numeral 46 designates a stopper formed on the supporting member 4 to limit the rotational range of the supporting arm 3. This stopper 46 is useful to prevent a situation that the position of the illumination unit 5 lowers more than necessary.

Figure 7:
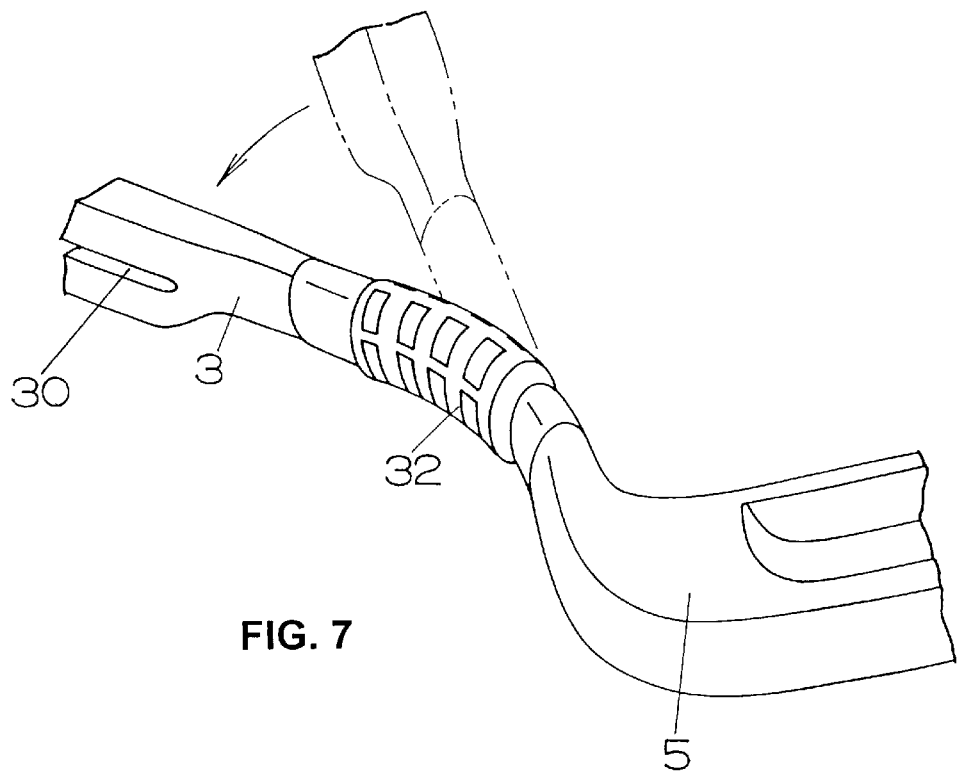
FIG. 7 is a partially perspective view of the supporting arm.
Figure 8:
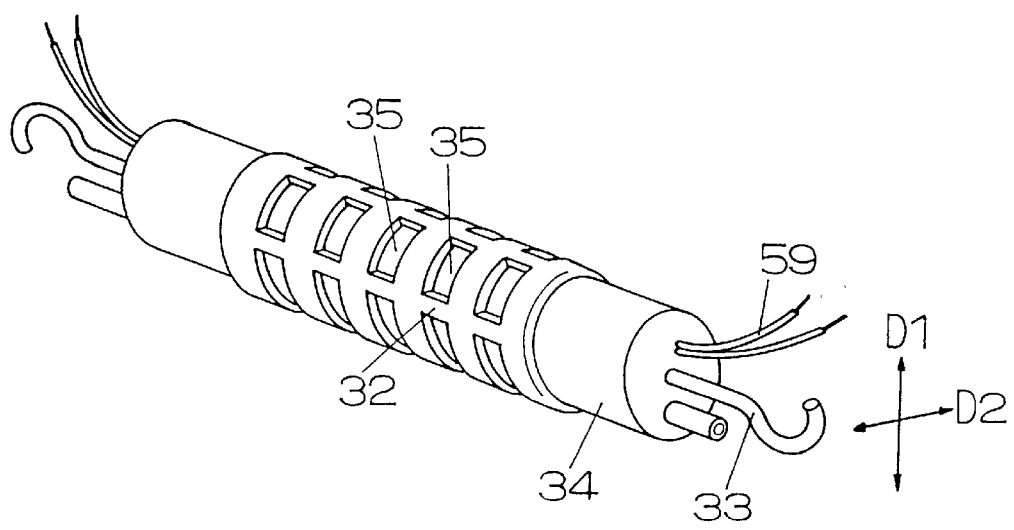
FIG. 8 is an exploded perspective view of a flexible portion of the supporting arm.

The supporting arm 3 has a flexible portion 32 at which the supporting arm can be flexibly bent. For example, even when the light irradiation device is used to a user with a relatively large head size, it is possible to comfortably put the light irradiation device on the user's head by bending the supporting arm 3 at the flexible portion 32, as shown by the arrow in FIG. 7. A detail structure of this flexible portion 32 is shown in FIG. 8. The flexible portion 32 is composed of a core member 33 made of a metal having excellent deformation capability, i.e., copper, and a soft material member 34 made of rubber or a soft synthetic resin which is integrally molded with the core material. In addition to the core member 33, electric wires 59 extending from the illumination unit 5 are embedded in the soft material member 34. To prevent a breakage caused in the electric wires 59 by the deformation of the flexible portion 32, the integrally molding is performed such that the electric wires and the core member 33 are not bonded to the soft material member 34. On the surface of the flexible portion 32, there are a plurality of concaves 35 for improving the deformation capability. As an example, the flexible portion 32 shown in FIG. 8 has twenty concaves 35, in which five concaves are evenly spaced in the longitudinal direction of the flexible portion, and four concaves are evenly spaced along the circumference of the flexible portion. It is preferred that the soft material member 34 has an ellipse cross-section to provide the dependence of deformation direction so that the supporting arm 3 can be easily bent in a direction (D2 in FIG. 8) of the small diameter of the ellipse rather than the direction (D1 in FIG. 8) of the large diameter of the ellipse.

Figure 9:
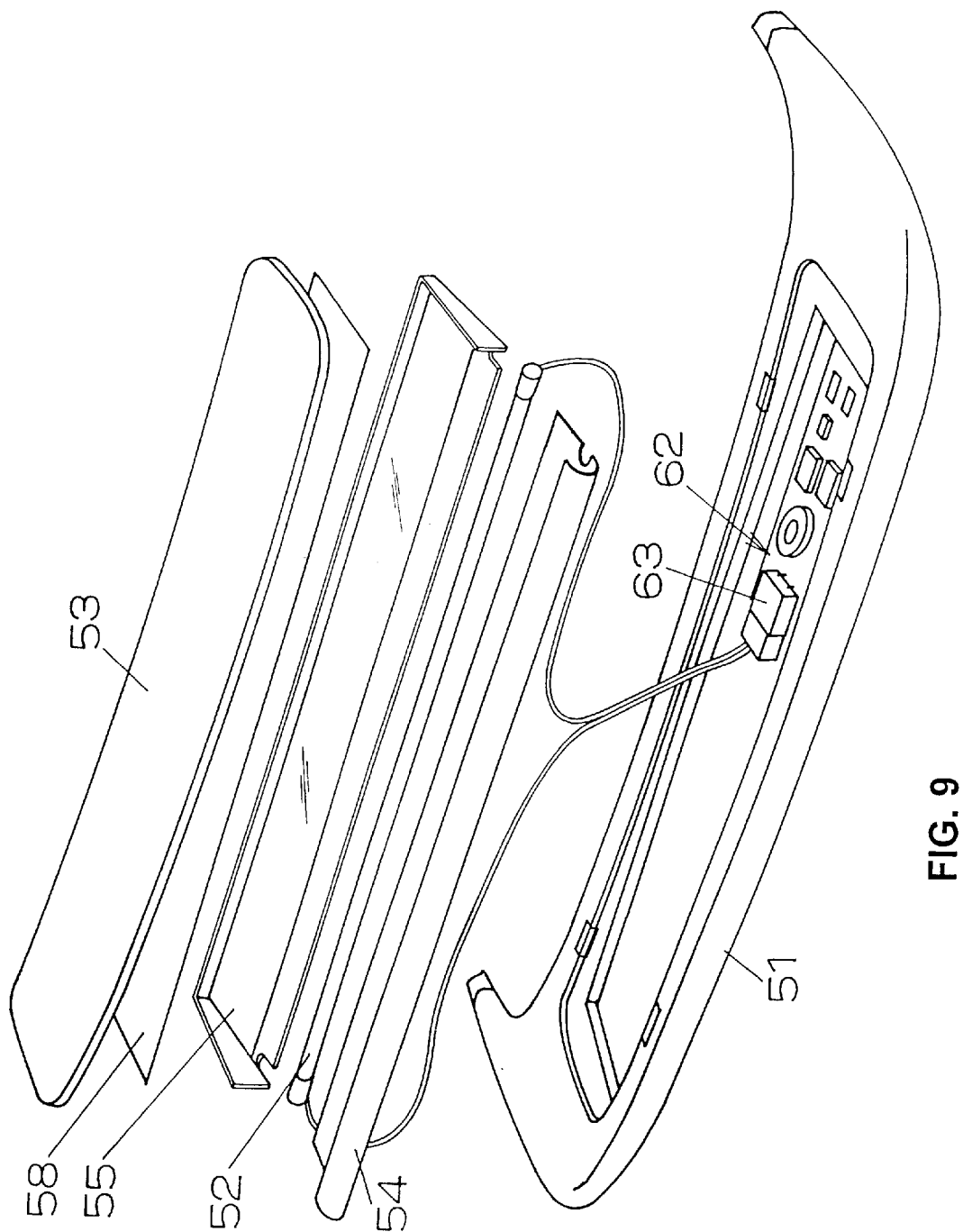
FIG. 9 is an exploded perspective view of an illumination unit of the light irradiation device.
Figure 10:
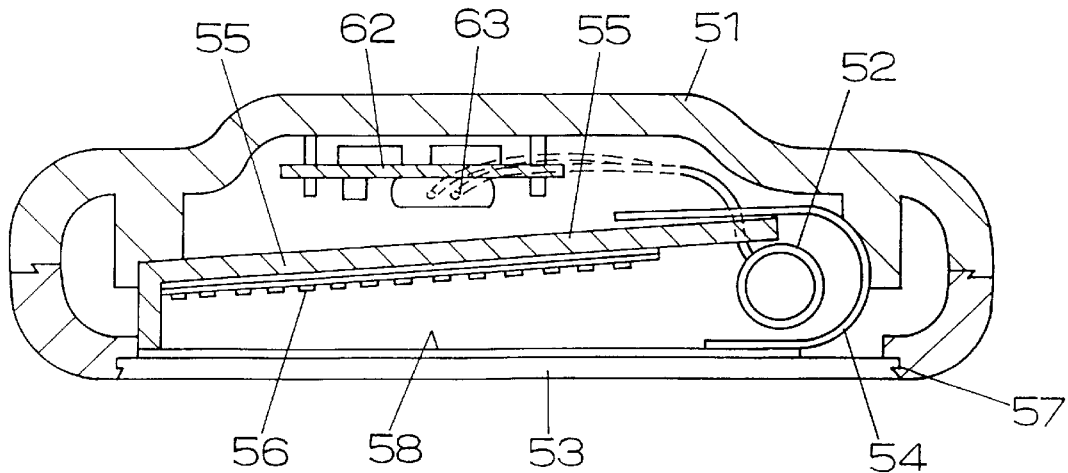
FIG. 10 is a cross-sectional view of the illumination unit of the light irradiation device.
Figure 11:
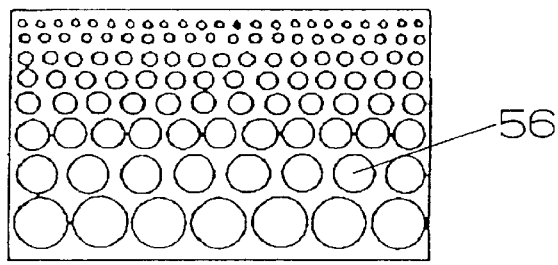
FIG. 11 is an example of a reflection-diffusing pattern.

The illumination unit 5 connected to the supporting arm 3 is shown in FIGS. 9 and 10. The illumination unit 5 includes a housing 51 having an aperture, rodlike light source 52 such as a cold-cathode tube having a diameter of 2 to 3 mm, light diffusing member 53 attached to the aperture of the housing, and a reflector placed at the opposed side to the light diffusing member through a space in the housing. The light diffusing member 53 diffuses the reflection from the reflector to provide the diffusion light to the user's eyes. The reflector is provided with a light-source protector 54 and a light reflecting portion 55. The light source can be exchanged by removing the light-source protector 54, and separating the light source 52 from a connector 63 of a printed circuit board 62 including a lighting circuit fixed in the housing 51. Another purpose of the light-source protector 54 is to avoid a situation that the light supplied from the light source 52 is irradiated to the user's eyes through the light diffusing member 53 and not through the light reflecting portion 55. To improve the reflectivity and prevent nonuniform brightness, it is preferred to use the reflector made of a whitely-painted material or an inherent white material. As shown in FIG. 10, there is a light introducing space filled with air between the light diffusing member 53 and the light reflecting portion 55 of the reflector. In the light introducing space, as a distance from the light source increases, the space between the light diffusing member 53 and the light reflecting portion 55 becomes narrower. This light introducing space filled with the air enhances the weight reduction of the illumination unit 5, and also prevent a decrease in light efficiency as compared with the case that an acrylic plate is inserted in the space between the light diffusing member and the light reflecting portion. A diffused reflection pattern 56 is formed on a surface of the light reflecting portion 55 such that as the distance from the light source increases, an effective diffused reflection area of the diffused reflection pattern is larger. As an example, the diffused reflection pattern 56 is shown in FIG. 1. The diffused reflection pattern can be obtained by printing a dot pattern on a polyethylene film or an acrylic thin film by use of an acrylic ink. Since the light diffusing member 53 has a hook 57 that can be engaged to a projection formed on the housing 51 at the vicinity of the aperture of the housing, the light diffusing member 53 can be readily removed from the housing and then exchanged to a different-type diffusing member on the user's own, if necessary. The light diffusing member 53 can be made of a milk-white color plate or sheet of a synthetic resin or a mat-finished translucent sheet (film). In FIG. 10, the numeral 58 designates a high-brightness diffusion sheet adhered on the back of the light diffusing member 53. The light provided from the light source 52 is provided to the outside through the light diffusing member 53.

A method of performing an optical medical treatment to the user by use of the light irradiation device of the present invention is explained below.

First, the user wears the light irradiation device on the head, while adjusting the effective lengths of the headband 10 and the auxiliary headband 13 to comfortably and stably fit those headbands on the top and rear portions of the user's head. In addition, the user allows the pads 2 to fit on the side portions of the user's head such that the first surface 20 of the respective pad 2 contacts the side portion at an adequate pressure by the spring force of the headband 10. With respect to each of the supporting arms 3, the projection length and projecting direction of the supporting arm relative to the fitted pad 2 on the user's head are adjusted by use of the above-explained click mechanisms to determine the most suitable position of the illumination unit 5 for the user. Next, the light source of the illumination unit 5 is turned on.

The light provided from the light source 52 is sent to the light diffusing member 53 through the reflector, so that a diffusion light is output from the surface of the light diffusing member. This diffusion light is a light having uniform brightness, and has a degree of brightness providing a sufficient amount of light stimulus to the user eyes without allowing the user to feel the glare of the diffusion light. For example, it is preferred that illumination at the position of eyeball is 2000 lux or more, and more preferably 3000 lux or more.

Since the light irradiation device of the present invention can be comfortably fitted on the user's head by use of the headband, auxiliary headband and the pads, it is possible to continue the optical medical treatment without allowing the user to feel the physically oppression to the user even when the optical medical treatment is performed over an extended time period, e.g., about 2 hours. In addition, since a suitable space is provided between the illumination unit and the user by use of the mechanisms of adjusting the projection length and the projecting direction of the supporting arm, it is possible to sufficiently exert the effect of the optical medical treatment without giving the psychological unpleasant feeling to the user.

Figures 13A, 13B:
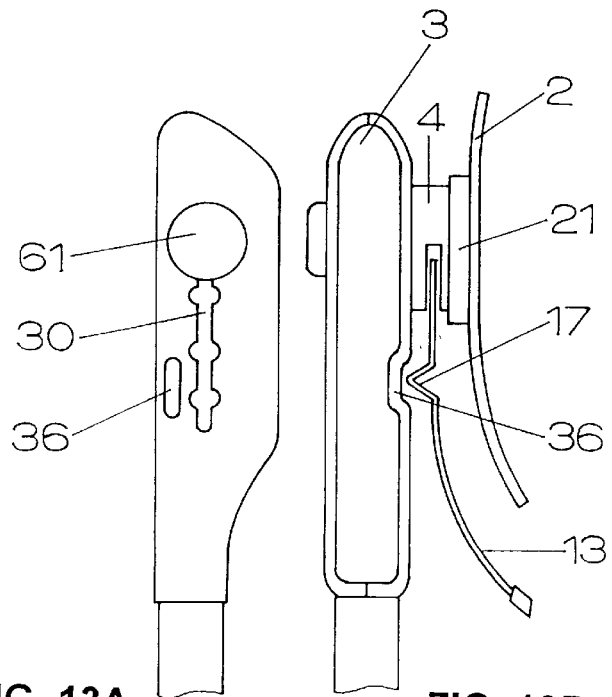
FIGS. 13A and 13B are plan views illustrating a locking mechanism between the auxiliary headband and the supporting arm.
Figure 12:
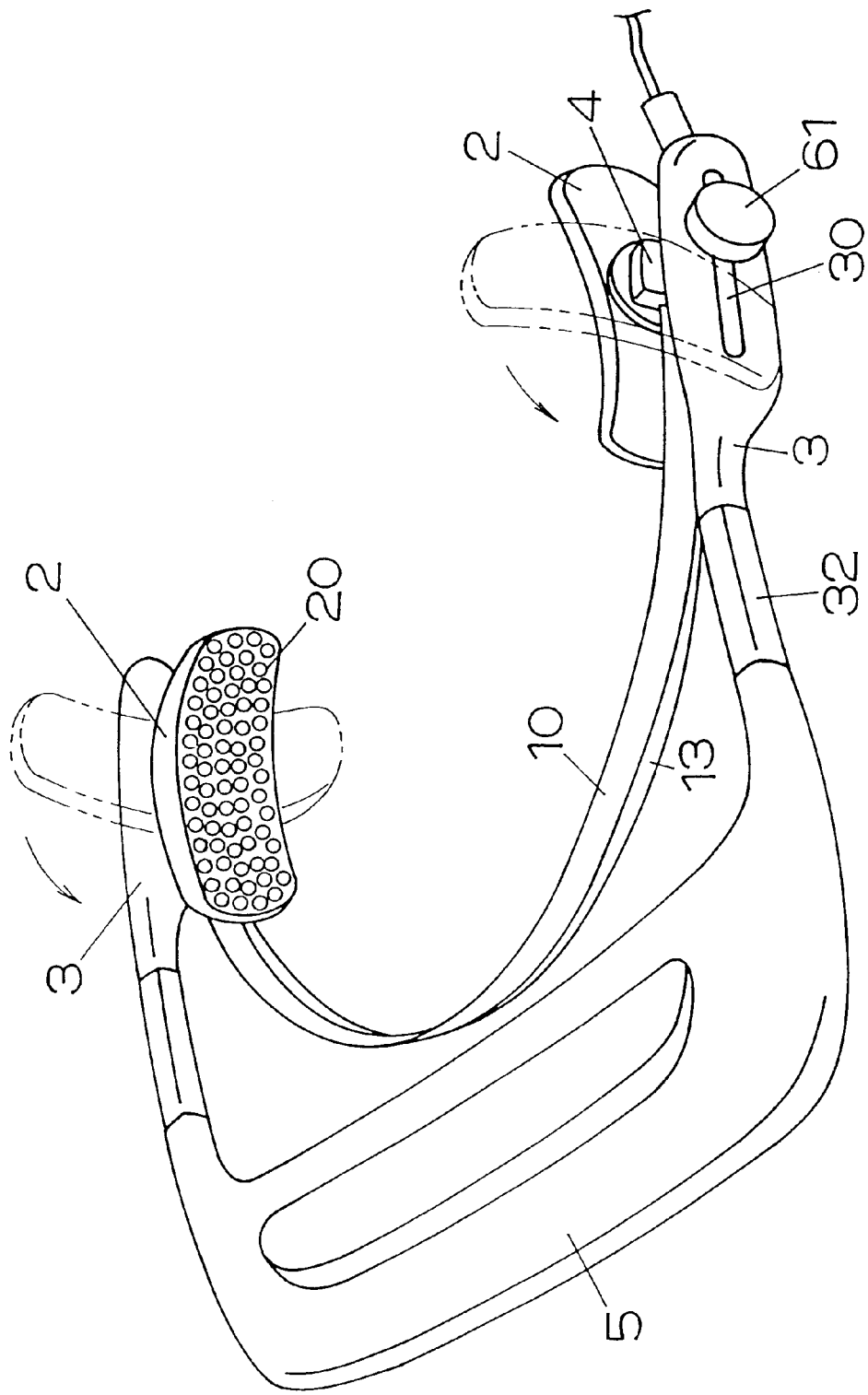
FIG. 12 is a perspective view illustrating a folding state of the light irradiation device of FIG. 1.

The light irradiation device of the present invention folds compact. That is, it is possible to fold the light irradiating device compact by rotating the supporting arms 3 and pads 2 relative to the supporting members 4 coupled with the headband 10, as shown in FIG. 12. By the way, the auxiliary headband 13 receives the spring bias in the direction away from the headband 10. However, as shown in FIGS. 13A and 13B, by engaging a projection 17 formed on the auxiliary headband 13 in a groove 36 formed near the second click groove 30 of the supporting arm 3, it is possible to hold the auxiliary headband adjacent to the headband against the spring bias at the folding state of the light irradiation device. This folding mechanism is useful to carry the light irradiation device to resolve jet lag during oversea travel, and will increase practical utility of the light irradiation device of the present invention.

In place of the projection-groove engagement mechanism explained above, the auxiliary headband 13 may be held adjacent to the headband 10 by friction between the auxiliary headband and the supporting member 4. For example, it is preferred to use a friction generating mechanism for generating a relatively large friction force between the auxiliary headband and the supporting member when the auxiliary headband is positioned adjacent to the headband. In this case, it is possible to prevent the travel of the auxiliary headband 13 in the direction away from the headband 10 by only the friction force without using the projection-groove engagement mechanism.

A portable light irradiation device of a second embodiment of the present invention is explained in detail.

Figure 14:
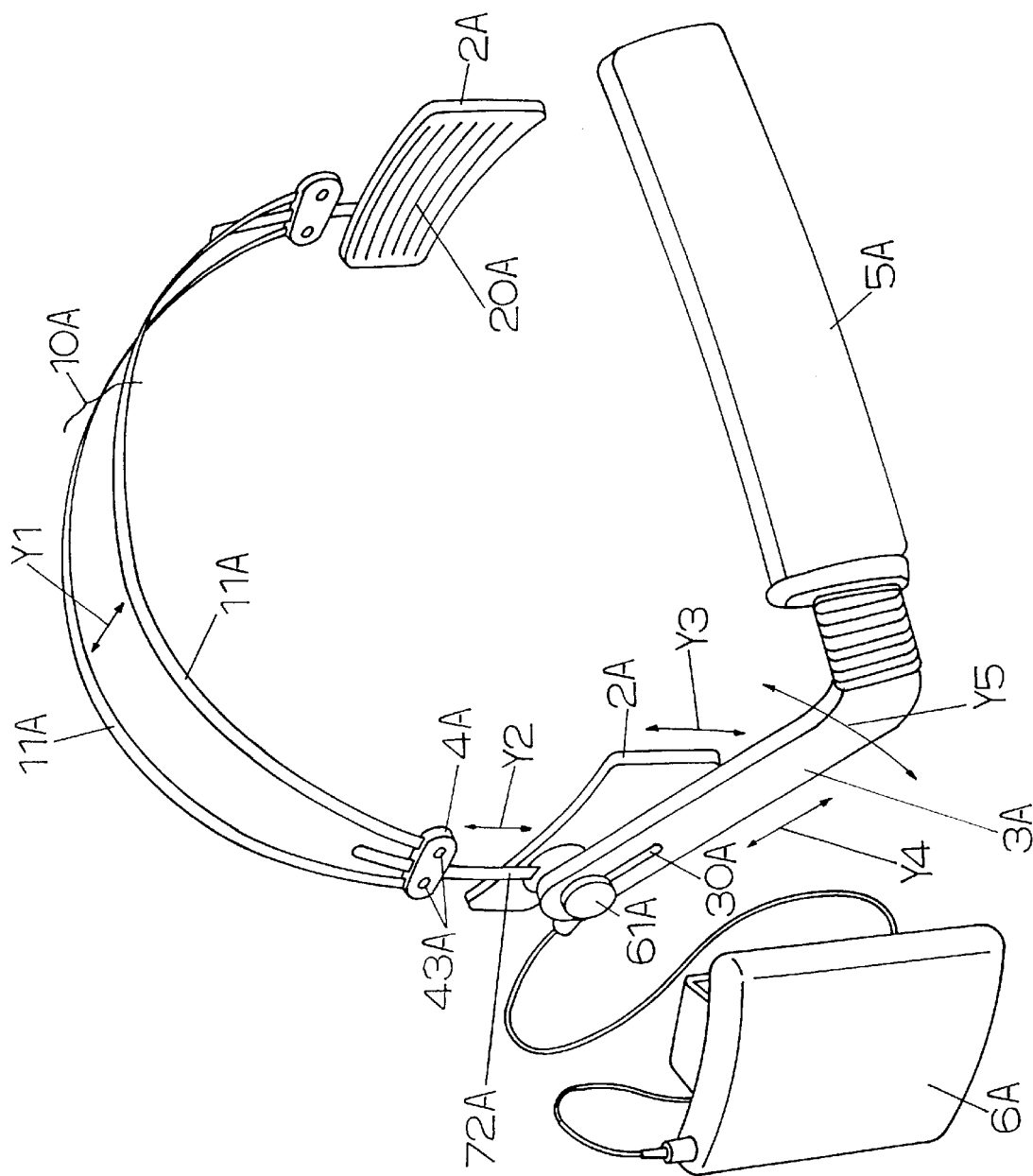
FIG. 14 is a perspective view of a light irradiation device of a second embodiment of the present invention.

As shown in FIG. 14, this light irradiation device includes a headband 10A, a pair of pads 2A, single supporting arm 3A and an illumination unit 5A. The numeral 6A designates a battery for supplying electric power to the illumination unit 5A.

Figure 15:
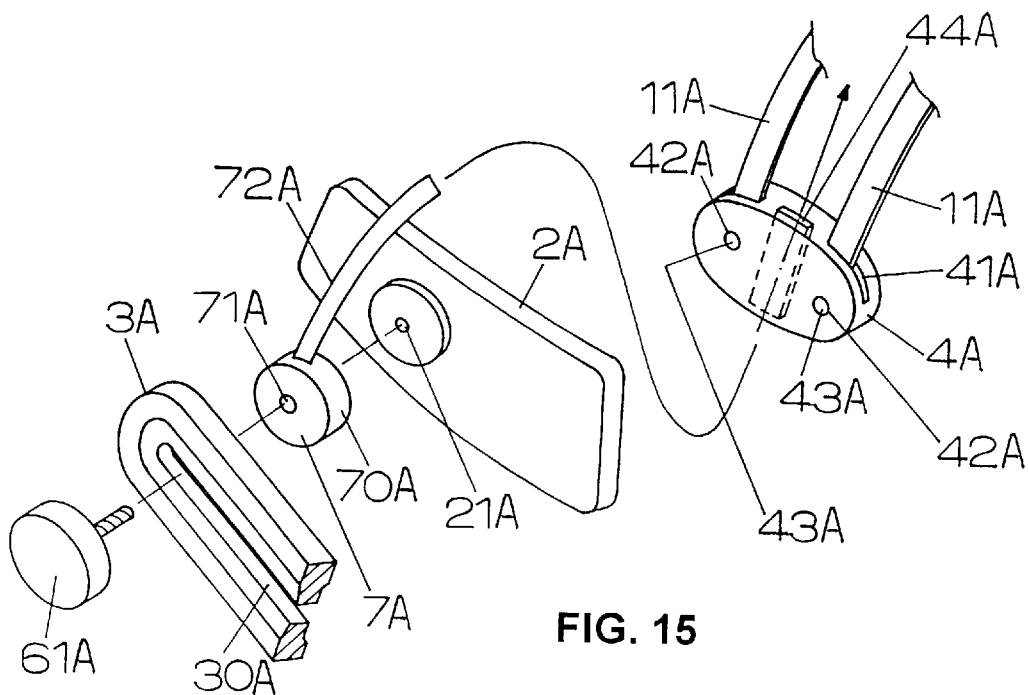
FIG. 15 is an exploded perspective view of a mechanism for coupling a supporting arm to a pad.

The headband 10A is formed with a pair of arcuate arms 11A made of a spring material. As shown in FIG. 15, end portions of the arcuate arms 11A are inserted into slits 41A of a supporting member 4A. Then, a shaft member 43A is inserted into a hole 42A of the supporting member 4A and a hole (not shown) formed in the end portion of the arcuate arm 11A, so that the arcuate arm is pivotally supported to the supporting member 4A about the axis of the shaft member.

That is, as shown by the arrow Y1 in FIG. 14, a space between the arcuate arms 11A is adjustable. By this adjustment of the space between the arcuate arms 11A, it is possible to suitably fit the headband 10A to the user's head.

The pads 2A are useful to further stably put the light irradiation device on the user's head. That is, each of the pads 2A has a first surface, which contacts a side portion of the user's head at an adequate pressure by a spring force of the arcuate arms 11A when the light irradiation device is put on the user's head. Each of the pads 2A is coupled to the supporting member 4A through a coupling member 7A. As shown in FIG. 15, the coupling member 7A is formed with a cylinder 70A having a hole 71A and an elongate sheet 72A projecting on a sidewall of the cylinder. The elongate sheet 72A of the coupling member 7A is inserted into a slot 44A formed in the supporting member 4A, and held by friction with the supporting member. Therefore, the elongate sheet 72A is slidably supported to the supporting member 4A in a direction shown by the arrow Y2 in FIG. 14. On the other hand, the cylinder 70A of the coupling member 7A is coupled to the pad 2A by use of a screw 61A. Therefore, the pad 2A can be rotated against the coupling member 7A about the axis of the screw 61A, as shown by the arrow Y3 in FIG. 14. The screw 61A makes a screw-engagement with a screw hole formed in the opposed surface to the first surface 20A of the pad 2A through the hole 71A of the cylinder 70A. Just fitting the headband 10A to the top portion of the user's head and comfortably fitting the pads 2A on the side portions of the head are achieved by the adjustment (Y1) of the space between the arcuate arms 11A, adjustment (Y2) of a distance between the coupling member 7A and the supporting member 4A, and the adjustment (Y3) of the pad position 2A. As a result, even when an optical medical treatment is performed for an extended time period, it is possible to concentrate the user's attention on the medical treatment while minimizing the physically oppressive feeling caused by putting the light irradiation device on the user's head.

As shown in FIG. 14, the illumination unit 5A is connected to an end of the supporting arm 3A, and the supporting arm is movably supported at the other end to the coupling member 7A by use of the screw 61A. That is, as shown in FIG. 15, the screw 61A makes the screw-engagement with the screw hole 21A of the pad 2A through a slit 30A formed in the end of the supporting arm 3A and the hole 71A of the coupling member 7A. By loosing the screw 61A, moving the supporting arm 3A in a direction shown by the arrow Y4 in FIG. 14, and tightening the screw at a desired position in the slit 30A of the supporting arm, it is possible to determine a projection length of the supporting arm 3A suitable for the individual user. In addition, it is possible to adjust a projecting direction of the supporting arm 3A against the pad 2A. That is, by loosing the screw 61A, pivotally moving the supporting arm 3A about the axis of the screw 61A, as shown by the arrow Y5 in FIG. 14, and tightening the screw 61A when the projecting direction of the supporting arm reaches a desired direction, it is possible to determine the projecting direction of the supporting arm suitable for the individual user. According to the above-explained adjusting mechanisms of the projection length and the projecting direction of the supporting arm, the illumination unit 5A can be set at a preferred angle to the user's eyes, and a suitable space between the illumination unit and the user's eyes can be determined. Therefore, it is possible to effectively perform the optical medical treatment to the user while minimizing the psychological unpleasant feeling caused when the illumination unit 5A excessively obstructs the user's view.

Figure 16:
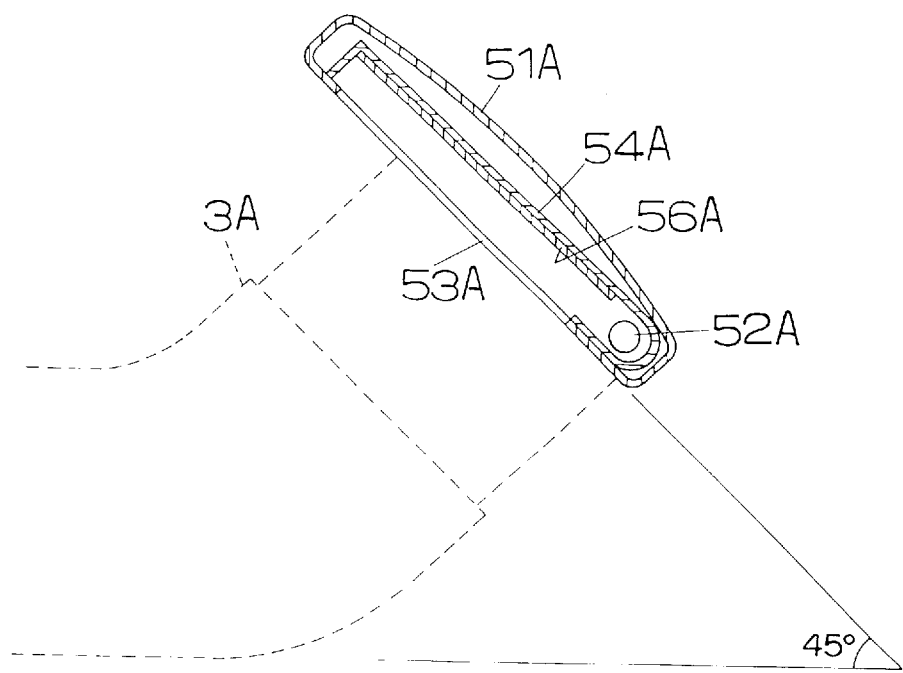
FIG. 16 is a cross-sectional view of an illumination unit.

As shown in FIG. 16, the illumination unit 5A connected to the supporting arm 3A includes a housing 51A having an aperture, rodlike light source 52A such as a cold-cathode tube having a diameter of 2 to 3 mm, light diffusing member 53A attached to the aperture of the housing, and a light reflecting plate 54A placed at the opposed side to the light diffusing member through a space in the housing. A light provided from the light source 52A is output to the outside through the reflecting plate 54A and the light diffusing member 53A. As shown in FIG. 16, it is preferred that an angle between a longitudinal axis of the supporting arm 3A and a general plane of the light diffusing member 53A is 45°. In the figure, the numeral 56A designates a diffused reflection pattern formed on a surface of the reflecting plate 54A.

Figure 17:
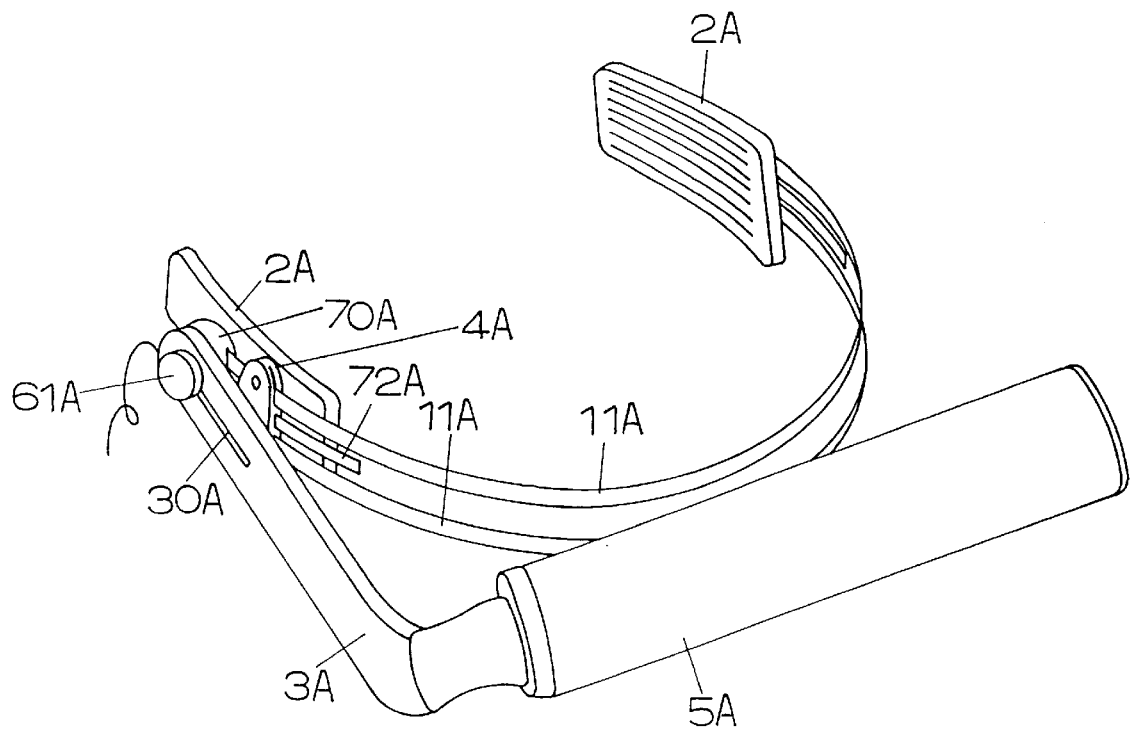
FIG. 17 is a perspective view illustrating a folding state of the light irradiation device of FIG. 14.

The light irradiation device of the present invention folds compact. That is, as shown in FIG. 17, it is possible to fold the irradiating device compact by rotating the supporting arms 3A and the pads 2A relative to the coupling member 7A coupled to the headband 10A through the supporting member 4A. This folding mechanism is useful to carry the light irradiation device to resolve jet lag during oversea travel, and will increase practical utility of the light irradiation device of the present invention.

Figure 18:
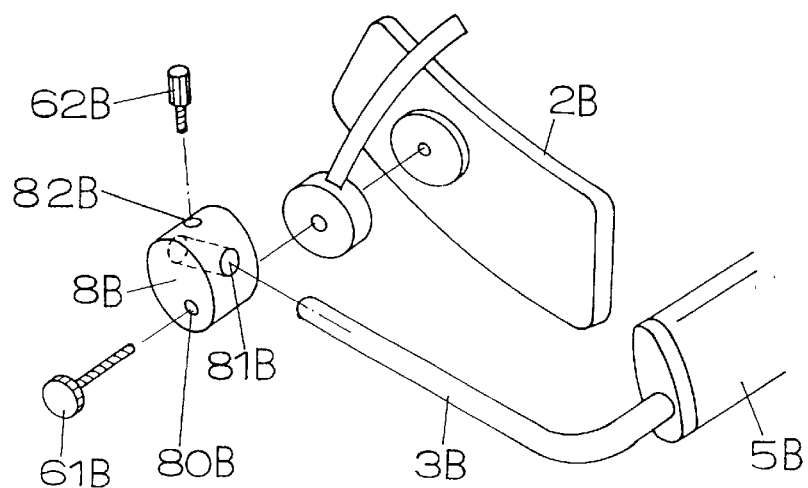
FIG. 18 is an exploded perspective view of an alternative mechanism for coupling the supporting arm to the pad.

A modification of the supporting arm 3A is shown in FIG. 18. In this case, a supporting arm 3B is a L-shaped rodlike arm, one end of which is connected to an illumination unit 5B. The other end of the supporting arm 3B is supported to a pad 2B through a cylindrically-shaped coupling member 8B. This coupling member 8B has a first hole 80B for passing a screw 61B, a second hole 81B for receiving the end of the supporting arm 3B, and a screw hole 82B used to secure the supporting arm inserted to the second hole 81B. In FIG. 18, the numeral 62B designates a screw for making a screw-engagement with the screw hole 82B. In this modification, it is possible to adjust a projecting direction of the supporting arm 3B relative to the pad 2B by loosing the screw 61B and rotating the coupling member 8B against the pad 2B about the axis of the screw 61B. It is also possible to adjust a projection length of the supporting arm 3B relative to the pad 2B by changing an insertion amount of the supporting arm into the second hole 81B of the coupling member 8B. The other components are substantially the same as those of the light irradiation device of the second embodiment.

Figure 19:
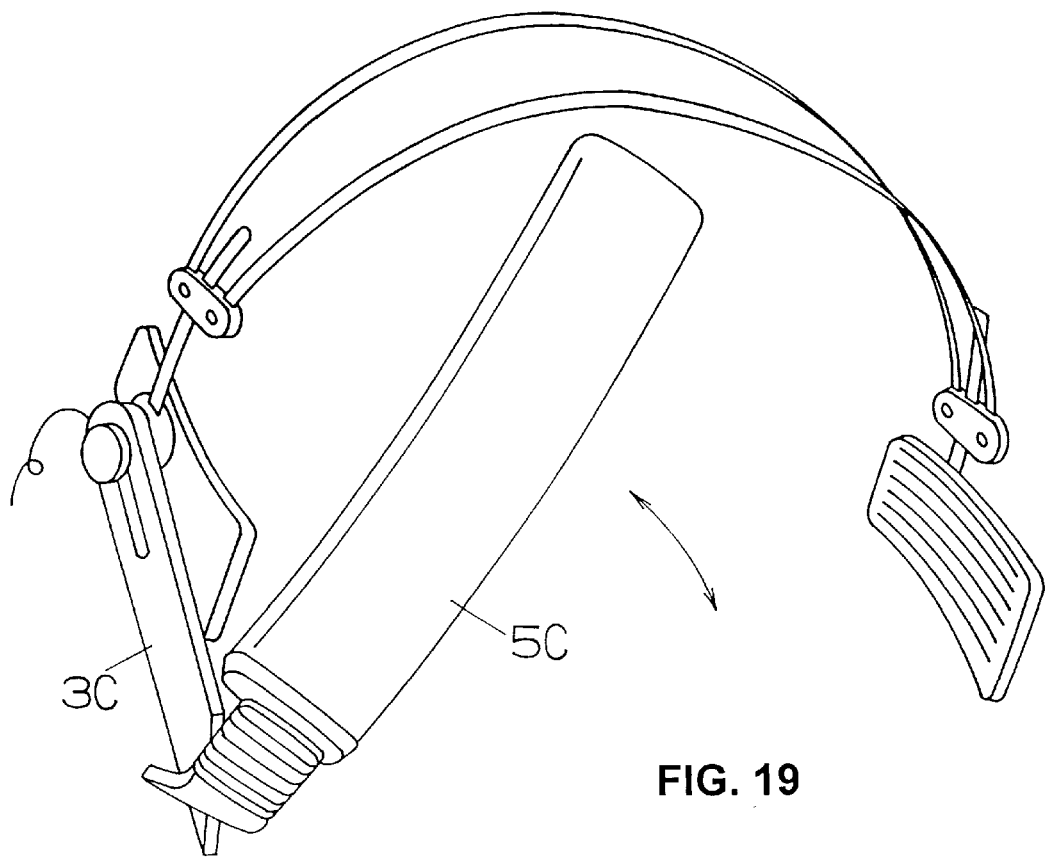
FIG. 19 is a perspective view of a light irradiation device of a modification of the second embodiment.
Figure 20:
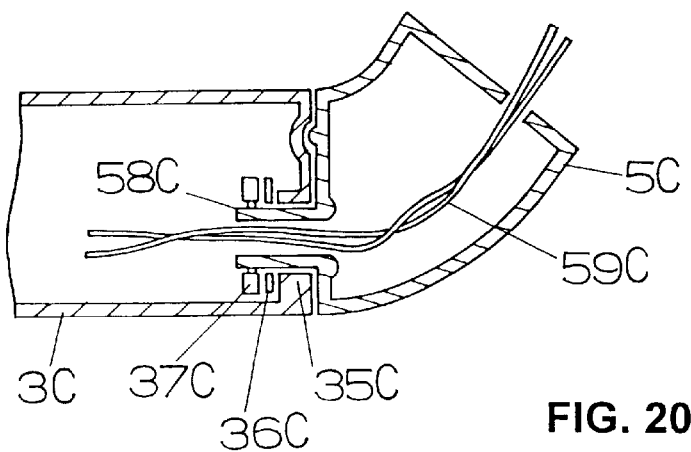
FIG. 20 is a cross-sectional view of another mechanism for coupling the illumination unit to the supporting arm.
Figure 21:
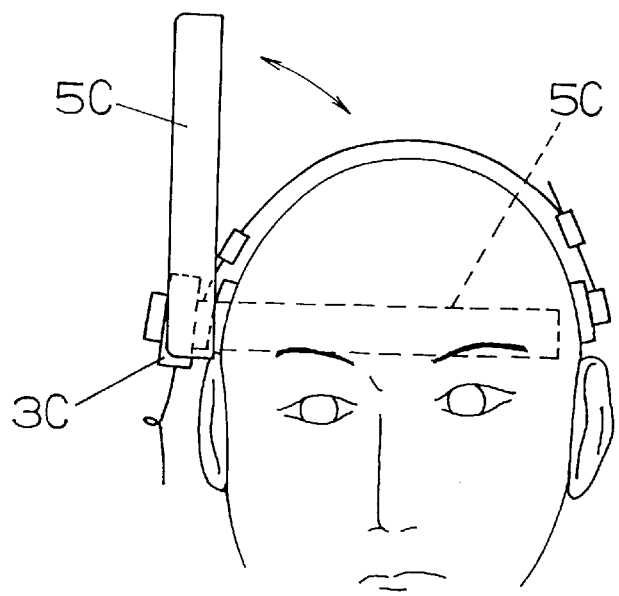
FIG. 21 is a plan view illustrating a fitting state of the light irradiation device of FIG. 19 to the user.

A further modification of the supporting arm 3A is shown in FIGS. 19 to 21. In this case, a supporting arm 3C is characterized by a connecting portion with an illumination unit 5C. That is, a bearing unit 35C is formed at a forward end of the supporting arm 3C. A shaft portion 58C formed at an end of the illumination unit 5C is movably supported by the bearing unit 35C such that the illumination unit 5C can be moved as shown by the arrow in FIG. 19. In the figure, the numeral 59C designates electric wires extending from the illumination unit 5C. The numerals 36C and 37C designates a washer and a nut, respectively. This coupling mechanism of the illumination unit 5C with the supporting arm 3C presents the following advantages. That is, when the light irradiation device is put on the user's head to provide the optical medical treatment, the illumination unit 5C is disposed at a substantially horizontal position slightly higher than the eye position of the user, as shown by the dotted line in FIG. 21. If necessary, it is possible to dispose the illumination unit 5C at a substantially vertical position by moving the illumination unit at the bearing unit 35C, as shown by the solid line in FIG. 21. For example, when the optical medical treatment is stopped for a brief period of time, and it is needed to revive the user's view, the user can easily remove only the illumination unit 5C from the front of the user's eyes by use of this coupling mechanism without removing the light irradiation device from the user's head. The other components are substantially the same as those of the light irradiation device of the second embodiment.

Figure 22:
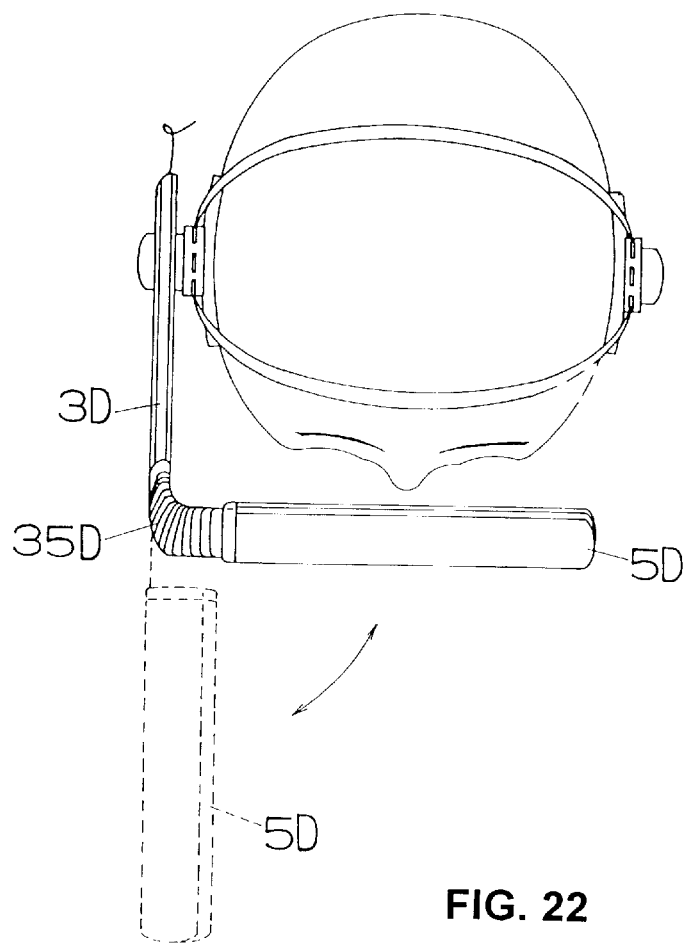
FIG. 22 is a plan view of a light irradiation device of a further modification of the second embodiment.

In addition, as shown in FIG. 22, in place of the above structure connecting between the bearing unit 35C and the shaft portion 58C, a flexible arm 35D may be used to connect between a supporting arm 3D and an illumination unit 5D. In this case, as described above, the user can readily remove the illumination unit 5D from the user's view by moving the illumination unit to the vertical position. In addition, the user can move the illumination unit 5D such that the supporting arm 3D and the illumination unit 5D are arranged in line, as shown by the dotted line in FIG. 22.

What is claimed is:

1. A portable light irradiation device for providing a stimulus of light to the eyes of user wearing said light irradiation device, said light irradiation device comprising:

an illumination unit of an elongate shape for irradiating said light to the user's eyes;

a pair of pads adapted to be fitted on both sides of the head of the user;

a headband adapted to be fitted to a top of the user's head, said headband coupled to said pads at opposite ends thereof; and a supporting arm extending from at least one of said pads to support said illumination unit at a forward end thereof so that said illumination unit can be disposed in front of the eyes of the user wearing the light irradiation device;

wherein said supporting arm is slidably supported to said pad at a rear end thereof such that a projection length of said supporting arm against said pad is adjustable, and has a flexible portion at which an angle of said illumination unit to said supporting arm is adjustable.

2. The light irradiation device as set forth in claim 1, further comprising a click mechanism for adjusting the projection length of said supporting arm against said pad in a stepwise manner, wherein said click mechanism includes a click spring member supported by said pad, and a slit formed in said supporting arm along a longitudinal direction of said supporting arm, and wherein said slit has a plurality of pockets arranged along the longitudinal direction, and said click spring member is movable within said slit so as to selectively make a click engagement with one of said pockets.

3. The light irradiation device as set froth in claim 1, wherein said supporting arm is rotatably supported to said pad at the rear end thereof such that a projection direction of said supporting arm against said pad is adjustable.

4. The light irradiation device as set forth in claim 1, wherein said supporting arm and said headband are rotatably supported to said pad to obtain a compact folding state of the light irradiation device.

5. The light irradiation device as set forth in claim 1, wherein said supporting arm is provided with a pair of supporting arms extending from said pads to opposite end portions of said illumination unit, and wherein each of said supporting arms has said flexible portion so that said spacing between said supporting arms is variable in accordance with a spacing between said pads.

6. The light irradiation device as set forth in claim 3, further comprising a click mechanism for adjusting the projection length of said supporting arm against said pad and a projection direction of said supporting arm against said pad in a stepwise manner, and wherein said click mechanism includes:

a click spring having a pair of first projections in a first direction and a pair of second projections in a second direction perpendicular to the first direction, said click spring made of an elastic material so that a distance between said first projections and a distance between said second projections are variable;

a coupling member supported by said pad, said coupling member having a pair of arcuate grooves formed around a horizontal axis extending between said pads, each of said arcuate grooves having a plurality of first pockets, so that each of said first projections of said click spring selectively makes a click-engagement with one of said first pockets of said arcuate groove; and a slit formed in said supporting arm along a longitudinal direction of said supporting arm, said slit having a plurality of pairs of second pockets, so that said second projections of said click spring selectively make a click-engagement with one pair of said second pockets.

7. The light irradiation device as set forth in claim 1, wherein said headband is slidably supported to said pads at opposite ends thereof so that an effective length defined as a length of said headband extending between said pads is adjustable.

8. The illumination device as set forth in claim 1, further comprising an auxiliary headband adapted to be fitted to a rear portion of the user's head, and wherein said auxiliary headband is swingably supported to said pads at opposite ends thereof.

9. The light irradiation device as set forth in claim 8, wherein said auxiliary headband is supported to said pads through spring members, and wherein said spring members provide a spring bias to said auxiliary headband in a direction away from said headband.

10. The light irradiation device as set forth in claim 8, wherein said auxiliary headband is fixable to said supporting arm at a position, where said auxiliary headband is spaced away from said headband by a horizontal distance so as to extend substantially parallel to said headband.

11. The light irradiation device as set forth in claim 8, wherein said supporting arm is a single supporting arm for supporting said illumination unit, and wherein said single supporting arm has said flexible portion at which an angle of said illumination unit to said supporting arm is adjustable.

12. The light irradiation device as set forth in claim 11, wherein said illumination unit is rotatable about a longitudinal axis of said supporting arm at said flexible portion of said supporting arm.

13. The light irradiation device as set forth in claim 1, wherein said illumination unit has a housing in which a light source, reflector for reflecting a light provided from said light source, light diffusing member for diffusing the reflection from said reflector to form a diffusion light and providing said diffusion light to the user's eyes, and a printed board including a lighting circuit for said light source are incorporated, and wherein said reflector, said light diffusing member, and said light source are detachable to said housing, and said light source is detachably connected to said lighting circuit by use of a plug-socket structure.

14. The light irradiation device as set forth in claim 1, wherein said illumination unit has a housing in which a light source, reflection plate for reflecting a light provided from said light source, light diffusing plate for diffusing the reflection from said reflector to form a diffusion light and providing said diffusion light to the user's eyes, and a protection cover for preventing exposure of said light source to the user's eyes through said light diffusion plate are incorporated., wherein a light introducing space filled with air is formed between said light diffusing plate and said reflection plate such that as a distance from said light source increases, spacing between said light diffusing plate and said reflection plate becomes narrower, and wherein a diffused reflection pattern is formed on a surface of said reflection plate such that as the distance from said light source increases, an effective diffused reflection area is larger.

* * * * *